United States Patent [19]

Inoue et al.

[11] Patent Number: 5,227,497

[45] Date of Patent: Jul. 13, 1993

[54] PROCESS FOR PREPARING $N^2$-(1-CARBOXY-3-PHENYLPROPYL)-L-LYSINE DERIVATIVE

[75] Inventors: Kenji Inoue, Hyogo; Satomi Takahashi, Kobe, both of Japan

[73] Assignee: Kanegafuchi Kagaku Kogyo Kabushiki Kaisha, Osaka, Japan

[21] Appl. No.: 810,082

[22] Filed: Dec. 19, 1991

Related U.S. Application Data

[62] Division of Ser. No. 630,801, Dec. 24, 1990, Pat. No. 5,136,044, which is a division of Ser. No. 333,145, Apr. 4, 1989, abandoned.

[30] Foreign Application Priority Data

Apr. 4, 1988 [JP] Japan .................................. 63-83632

[51] Int. Cl.$^5$ ............................................. C07C 207/08
[52] U.S. Cl. .................................................... 548/533
[58] Field of Search .......................................... 548/533

[56] References Cited

U.S. PATENT DOCUMENTS

| | | | |
|---|---|---|---|
| 4,716,235 | 12/1987 | Takahashi et al. | 548/533 |
| 4,837,332 | 6/1989 | Chou | 548/533 X |
| 4,847,384 | 7/1989 | Kapa et al. | 548/533 X |
| 4,960,881 | 10/1990 | Barcelo et al. | 548/533 X |
| 5,136,044 | 8/1992 | Inoue et al. | 548/227 |

*Primary Examiner*—Joseph Paul Brust
*Attorney, Agent, or Firm*—Armstrong, Westerman, Hattori, McLeland & Naughton

[57] ABSTRACT

A process for producing $N^2$-(1-(S)-carboxy-3-phenylpropyl)-L-lysil-L-proline of formula (VIII);

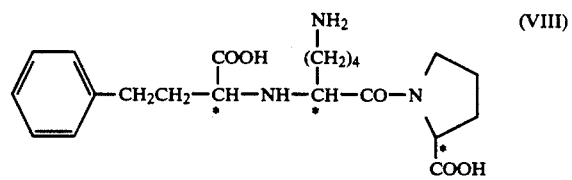

$N^2$-(1-substituted-3-phenylpropyl)-L-lysil-L-proline derivative of formula (VII);

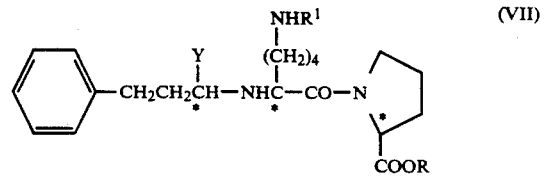

and $N^2$-(1-carbonyl-3-phenylpropyl)-L-lysil-L-proline derivative of formula (XXVI);

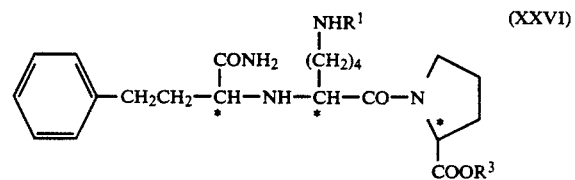

is disclosed.

7 Claims, No Drawings

PROCESS FOR PREPARING N²-(1-CARBOXY-3-PHENYLPROPYL)-L-LYSINE DERIVATIVE

This application is a division of application Ser. No. 07/630,801, filed Dec. 24, 1990, and now U.S. Pat. No. 5,136,044, which in turn is a division of application Ser. No. 07/333,145, filed Apr. 4, 1989 and now abandoned.

and N⁶-tert-butoxycarbonyl-L-lysil-L-proline (VII) with potassium cyanide (Strecker reaction) to form a compound shown by formula (X) below, successively treating the compound (X) with hydrogen chloride/methanol and an acid ion exchange resin to form a diester derivative shown by formula (XI) shown below, and further hydrolyzing the diester derivative (XI) with alkali as shown in the following reaction formula (JP-A-58-113158) (the term "JP-A" as used herein means an "unexamined published Japanese patent application");

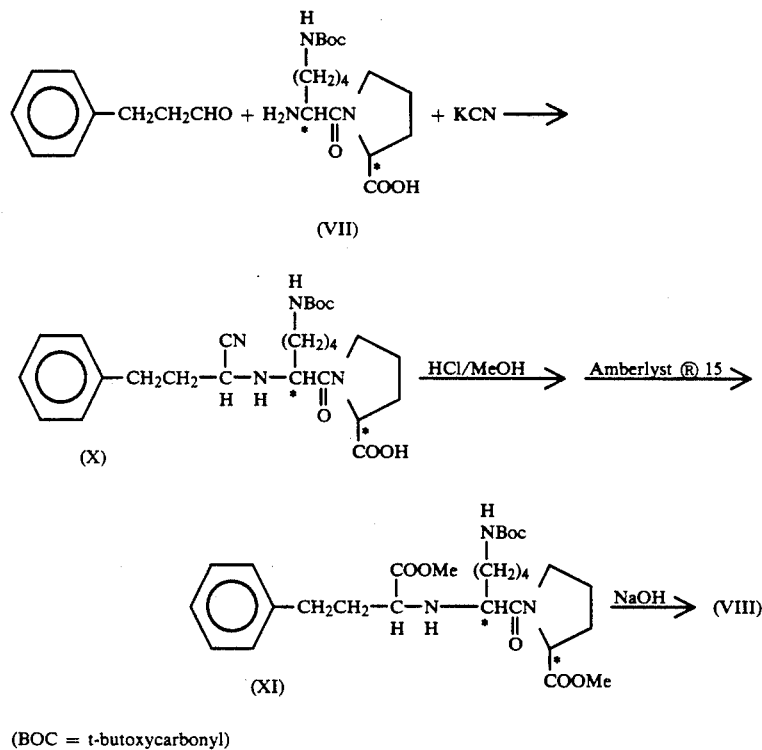

(BOC = t-butoxycarbonyl)

FIELD OF THE INVENTION

This invention relates to a process of effectively producing N²-(1-(S)-carboxy-3-phenylpropyl)-L-lysil-L-proline (lysinoprile) (VIII) using an N²-(1-cyano-3-phenylpropyl)-L-lysine derivative (V).

Lysinoprile (VIII) is a compound expected to be utilized as an antihypotensive agent owing to its excellent angiotensine conversion enzyme (ACE) inhibiting activity.

BACKGROUND OF THE INVENTION

As a process of producing lysinoprile (VIII), there is known a process of reacting β-phenylpropionaldehyde Also known is a process of reacting the N-carboxy anhydride of N⁶-trifluoroacetyl-L-lysine and L-proline to provide N⁶-trifluoroacetyl-L-lysil-L-proline shown by formula (XII) below, reductively alkylating the proline derivative (XII) with ethyl α-oxo-γ-phenylbutyrate (XIII) to form N⁶-(1-ethoxycarbonyl-3-phenylpropyl)-L-lysil-L-proline shown by formula (XIV) below, and then hydrolyzing th proline derivative (XIV) with alkali as shown by the following reaction formula (JP-A-61-36297).

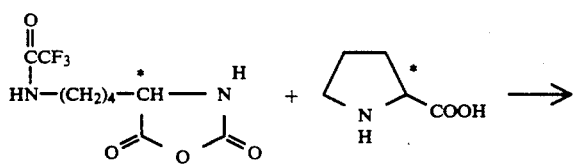

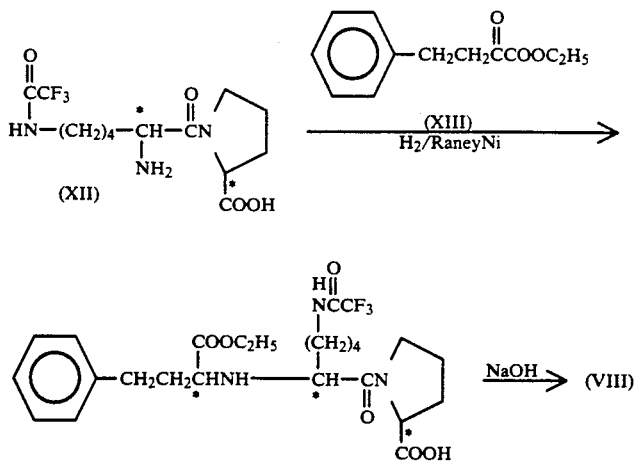

However, the materials or pigments used in the aforesaid processes except β-phenylpropionaldehyde, L-proline, and potassium cyanide have the following disadvantages. That is, they have complicated structures, can be not always easily available, are expensive and require considerable many steps for the synthesis thereof. Also, for obtaining an isomer having an absolute configuration inevitable for that (S,S,S) lysinoprile shows an activity as an angiotensine conversion enzyme inhibitor (ACEI), it is desirable to separate starting materials, inclusive of intermediate, so as to obtain the final product in high purity since the starting material are expensive and may be easily separated through an optical resolution. Thus, the aforesaid processes have difficulties in economy and operability as a practical production process of lysinoprile.

The inventors previously discovered a process of efficiently producing α-(1-carboxyethyl)amino-γ-phenylbutyric acid ethyl esters which are very useful as the intermediates for producing many ACEIs by using Strecker reaction using inexpensive starting materials as described in Japanese Patent Application No. 62-204860.

SUMMARY OF THE INVENTION

As the result of investigations for developing a process of efficiently producing lysinoprile (VIII) based on the aforesaid technique, the inventors have discovered a novel process of efficiently producing lysinoprile (VIII) using, as an intermediate, an α-(1-cyano-3-phenylpropyl)-L-lysine derivative which can be easily produced by subjecting β-phenylpropionaldehyde and an L-lysine derivative (IV), which are inexpensive and easily available raw materials, to a so-called Strecker reaction in the existence of a cyanating agent and have succeeded in attaining the present invention.

The reaction scheme of the process of this invention is as follows.

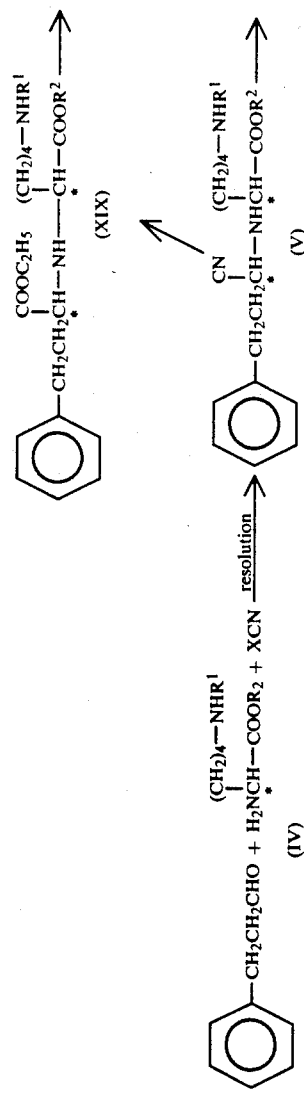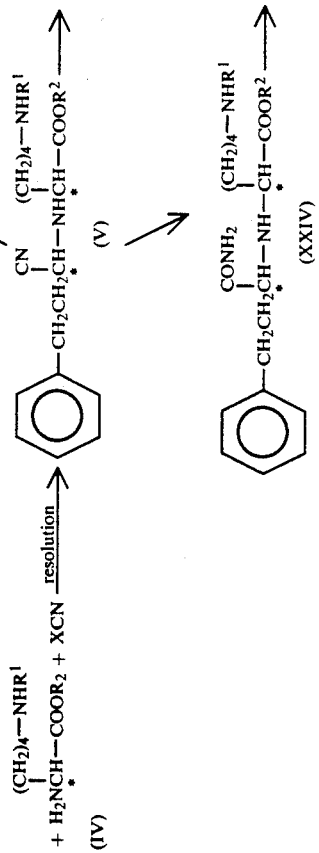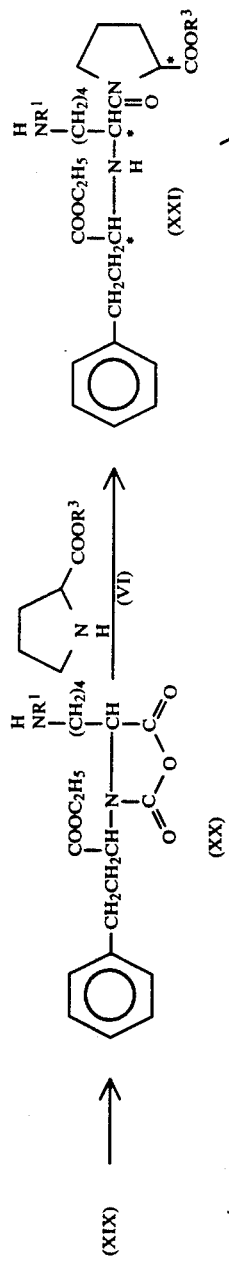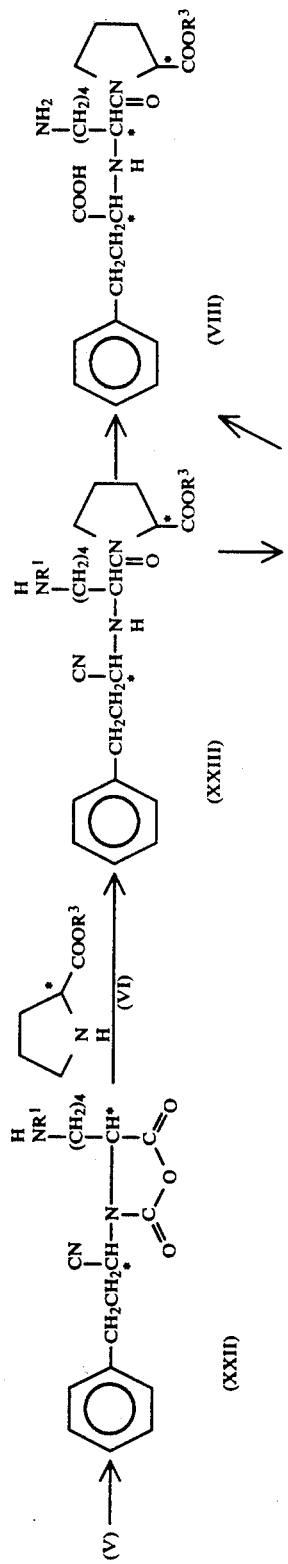

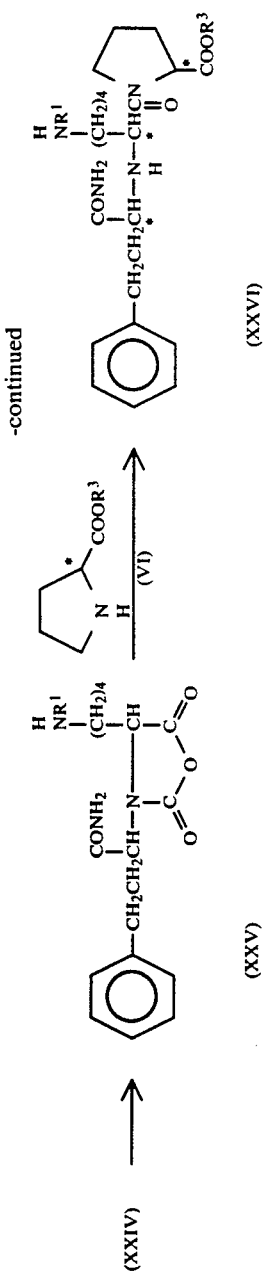

In the aforesaid reaction formula, $R^1$ represents an acyl type or urethane type protective group; $R^2$ represents a hydrogen atom, an alkyl group, or an aralkyl group; and the mark * represents the S-position of the asymmetric carbon atom.

That is, it has now been clarified that an $N^2$-(1-substituted-3-phenylpropyl)-L-lysyl-L-proline (XXIII) or (XXVI) can be produced by treating an $N^2$-(cyano-3-phenylpropyl)-L-lysine derivative (V), (which is a novel compound capable of being easily produced from phenylpropionaldehyde, a L-lysine derivative, and a cyanating agent as it is or after converting (V) to an amide derivative (XXIV) by an acid hydrolysis, followed by treating (XXIV) with phosgene, etc., to form an N-carboxy anhydride (XXII) or (XXV), and reacting the N-carboxy anhydride and an L-proline (VI) in the presence of a base; that the compound (XXIII) or (XXVI) can be easily converted into lysinoprile (VIII); that an $N^2$-(1-ethoxycarbonyl-3-phenylpropyl)-L-lysine derivative (XIX) can be produced by treating an $N^2$-(1-cyano-3-phenylpropyl)-L-lysine derivative (V) with HCl/ethanol and hydrolyzing the imidate thus formed; and that an $N^2$-(1-ethoxycarbonyl-3-phenylpropyl)-L-lysyl-L-proline derivative (XXI) can be easily obtained by treating the $N^2$-(1-ethoxycarbonyl-3-phenylpropyl)-L-lysine derivative (XIX) with phosgene, etc., to provide an N-carboxy anhydride (XX), and then reacting the N-carboxy anhydride and proline under a basic condition.

Also, it has been clarified that lysinoprile (VIII) can be advantageously produced by finding that the desired 1-S compound can be predominantly produced in asymmetric induction by controlling the synthesis condition of the α-(1-cyano-3-phenylpropyl)-L-lysine derivative (V) in the aforesaid case as compared with the 1-R compound, and that the 1-S L-lysine derivative (IV) can be easily separated from the 1-R lysine derivative (V), and the invention has been accomplished based on the finding.

DETAILED DESCRIPTION OF THE INVENTION

As the lysine component (IV) in the production of the $N^2$-(cyano-3-phenylpropyl)-L-lysine derivative (V), L-lysine derivatives the ε-amino group of which is protected by a protective group being usually used for the synthesis of peptide, and the esters and salts can be used. As the protective group being used for the purpose, there are a substituted benzyloxycarbonyl group such as a tertiary butyloxycarbonyl group, a benzyloxycarbonyl group, a p-nitrobenzyloxycarbonyl group, etc.; a urethane type protective group such as an isobornyloxycarbonyl group, etc.; and an acyl type protective group such as a trifluoroacetyl group, a formyl group, a phthaloyl group, etc.

Also, as the salt of the protected S-lysine derivative with a base, there are alkali metal salts thereof such as lithium salts, sodium salts, potassium salts, etc., and quaternary ammonium salts thereof. As the esters of the protected S-lysine derivative, there are esters which are usually utilized for the synthesis of peptide, such as the esters of an alkyl group (e.g., methyl, ethyl, n-propyl, iso-propyl, n-butyl, tertbutyl, cyclohexyl, and trichloroethyl) and the esters of an aryl group (e.g., phenyl).

On the other hand, as the cyano compound, there are cyanating agents which are usually used for the synthesis of aminonitrile, such as hydrocyanic acid, sodium cyanide, potassium cyanide, acetone cyanhydrin, trimethylsilyl cyanide, etc.

In the case of using the lysine derivative and the cyano compound, there is, as a matter of course, an advantageous combination. For example, in the case of using the salt of the protected S lysine with acid or the salt of the protected S-lysine ester with an acid, a combination with an alkali metal cyanide is effective and in the case of using the salt of the protective L-lysine with a base or the salt of the protected L-lysine ester with a base, a combination with hydrocyanic acid, acetone cyanhydrin, or trimethylsilyl cyanide is effective. However, the invention is not limited to such combinations since in the case of controlling the acid-base balance by adding an acid or a base to the reaction system, and other various combinations may be also employed.

For producing the $N^2$-(1-cyano-3-phenylpropyl)-L-lysine derivative (V), there are, for example, i) a process of simultaneously reacting the three components, i.e., phenylpropionaldehyde, an L-lysine components, and a cyano compound;

ii) a process of first synthesizing a cyanhydrin compound from phenylpropionaldehyde and a cyan compound by an ordinary manner and then reacting the cyanhydrin with a lysine component; and iii) a process of first obtaining a so-called Schiff base from phenylpropionaldehyde and a lysine component and then adding thereto a cyan compound.

Also, as the reaction condition for the aforesaid processes, a general condition in an ordinary synthesis of aminonitrile can be employed.

That is, in process i), the reaction is carried out at a temperature of from 0° C. to 50° C. In process ii), cyanohydrin is obtained by reacting phenylpropionaldehyde and hydrocyanic acid in the existence of a base at a temperature of from 0° C. to 60° C. or reacting a phenylpropionaldehyde-sodium hydrogensulfite addition product and an alkali metal cyanide at about room temperature and reacting the cyanhydrin and a lysine component at a temperature of from 0° C. to 50° C. Also, in process iii), the Schiff base is formed by reacting phenylpropionaldehyde and a lysine component in an anhydrous solvent under the existence of an ordinary dehydrating agent such as molecular sieve and anhydrous magnesium sulfate at a temperature of from 0° C. to 100° C., and preferably from 10° C. to 30° C. and then the Schiff base is reacted with hydrocyanic acid, a cyanide, trimethylsilyl cyanide, etc., under cooling to provide the aminonitrile compound.

The aforesaid reactions, except the case of forming the Schiff base in process iii), each can be usually carried out in water, an organic solvent, or a mixture thereof.

As the organic solvent, there are alcohols such as methanol, ethanol, isopropanol, etc.; nitriles such as acetonitrile, propionitrile, etc.; ethers such as diethyl ether, dioxane, tetrahydrofuran, etc.; amides such as dimethylformamide, hexamethylphosphoramide, etc.; and halogenated hydrocarbons such as methylene chloride, chloroform, etc.

The conditions for predominantly producing the (S,S) isomers as compared to the (R,S) isomers in the reaction differs according to the process being employed from the aforesaid processes i), ii), and iii), but in the case of using, for example, process i), the $N^2$-(1(S)-cyano-3-phenylpropyl)-L-lysine derivative can be predominantly obtained to the 1-R isomer by successively mixing phenylpropionaldehyde, sodium cyanide, and an L-lysine component in a protonic solvent such as water, methanol, ethanol, isopropanol, etc., solely or as a mixture thereof with other solvent under stirring at a temperature of from −40° C. to 80° C., and preferably from 0° C. to 50° C. for from 50 hours to 5 minutes.

For obtaining the 1-S isomer only from the mixture of the isomers of $N^2$-(1-cyano-3-phenylpropyl)-L-lysine thus obtained, various methods being employed for an ordinary resolution of a diasteromer can be employed and, for example, the crystals of the 1-S isomer can be easily obtained by recrystallizing from a mixture of water and methanol.

The conversion of the $N^2$-(1(S)-cyano-3-phenylpropyl)-L-lysine derivative (V) into the amide derivative (XXIV) can be easily carried out by using a mineral acid such as hydrochloric acid, sulfuric acid, etc., according to an ordinary manner and the conversion can be attained by reacting them at a temperature of from −10° C. to 80° C., and preferably from 0° C. to 50° C. for from 40 hours to 5 minutes. In this case, for inhibiting the occurrence of side-reaction such as splitting a peptide bond it is preferred to carry out the reaction at a low temperature of from 0° C. to 30° C. using sulfuric acid as the mineral acid in the presence of water in an amount of from 0.1% to 100%, and preferably from 1% to 50% of sulfuric acid.

The conversion of the $N^2$-(1(S)-cyano-3-phenylpropyl)-L-lysine derivative (V) into the ethyl ester derivative (XIX) can be carried out by an ordinary process of converting a cyano group into the ester group thereof. For example, the $N^2$-(1(S)-ethoxycarbonyl-3-phenylpropyl)-L-lysine derivative (XIX) can be obtained by reacting the L-lysine derivative (V) in a saturated ethanol solution of dry hydrogen chloride gas at a temperature of from −30° C. to 30° C., and preferably from 0° C. to 10° C. for from 40 hours to 1 hour and hydrolyzing the imidate thus formed with water.

The conversion of the $N^2$-(1(S)-substituted-3-phenylpropyl)-L-lysine derivative (XIX), (V), or (XXIV) into the N-carboxy anhydride can be carried out by the same procedure as the case of a general synthesis of the N-carboxy anhydride of α-amino acid as described in JP-A-57-175152 and JP-A-62-48696 after decomposing the ester by an ordinary method using an acid, a base, or hydrogenolysis when the L-lysine component has an ester group.

That is, the aforesaid conversion can be easily performed by refluxing the L-lysine derivative (XIX), (V), or (XXIV) in methylene chloride containing phosgene or by heating the derivative together with trichloromethyl chloroformate in an inert solvent in the presence of a small amount of active carbon.

The reaction for forming the peptide bond of the N-carboxy anhydride thus obtained and L-proline can be easily attained by mixing L-proline and the N-carboxy anhydride in the existence of a base as described in JP-A-62-48696.

As the base for use in the aforesaid reactions, there are inorganic bases such as hydroxides, carbonates, and hydrogencarbonates of alkali metals such as lithium, sodium, and potassium; hydroxides of alkaline earth metals such as calcium and magnesium; as well as amines excluding primary amines, e.g., secondary amines such as dimethylamine, diethylamine, diethanolamine, dichlorohexylamine, etc., tertiary amines such as trimethylamine, triethylamine, tripropylamine, tributylamine, triamylamine, triethanolamine, pyridine, N-alkylmorpholine, etc., and tetramethyl, tetraethyl, tetrapropyl, tetrabutyl, tetraamyl, tetrahexyl, benzyltrimethyl, and benzyltriethyl quaternary ammonium hydroxides, etc.

The peptide bond forming reaction can be carried out in an aqueous medium, particularly preferably in a mixed system of water and an organic solvent. In this case, a mixed system of water and an organic solvent having a high compatibility with water, such as acetone, dioxane, tetrahydrofuran, acetonitrile, and lower alcohols can be advantageously utilized.

A solvent having a low compatibility with water, such as ethyl acetate, methylene chloride, chloroform, hexane, ether, etc., is generally slow in reaction rate and is inferior in yield but even if the case of using such a solvent, the reaction rate can be increased and the yield can be improved by vigorously stirring the mixed system and controlling the pH to a definite value.

The aforesaid reaction can be carried out by adding to an L-proline a base in an equimolar amount thereto or an amount of slightly excessive thereto to form previously a salt of proline and adding a solution of the N-carboxy anhydride dissolved in an organic solvent to the solution containing the salt of proline thus formed with stirring under cooling. However, the reaction in this product by an organic solvent such as methylene chloride, and then concentrating the extract under reduced pressure.

The $N^2$-(1-substituted-3-phenylpropyl)-L-lysil-L-proline derivative (XXI), (XXIII), or (XXVI) can be easily converted into lysinoprile (VIII) by an acid or alkali hydrolysis.

Then, the following examples are intended to illustrate the present invention not to limit it in any way.

In addition, the quantitative analysis in the examples was carried out by a high performance liquid chromatography (HPLC).

Also, the following conditions were used for the analysis.

Column:

Finepak SIL $C_{18-5}$ (made by Nippon Bunkoo K.K.) 4.6 mm ID×250 mm.

Transfer Phase 60 mM phosphoric acid buffer (pH 2.5)/acetonitrile=55/45 to 80/20 (V/V).

Flow Rate: 1.5 ml/min, 1 ml/min.

Detection: 210 n.m.

The present invention is hereinafter described in greater detail with reference to the following examples, which are not to be construed as limiting the scope thereof.

EXAMPLE 1

Synthesis of $N^2$-(1(S)-cyano-3-phenylpropyl)-$N^6$-trifluoroacetyl-L-lysine

In 420 ml of methanol was dissolved 6.2 g of sodium cyanide and after further adding dropwise 29.4 g of $N^6$-trifluoroacetyl-L-lysine and further 16.1 g of β-phenylpropionaldehyde to the solution, the resultant mixture was stirred for 16 hours at room temperature. After the reaction was over, 10 ml of concentrated hydrochloric acid was slowly added to the reaction mixture and after adding thereto 420 ml of water, the mixture was stirred for 10 minutes at room temperature. The crystals thus deposited were recovered by filtration, washed with 100 ml of water, and dried in vacuo at 80° C. to provide 22.6 g of the crystals of $N^2$-(1-cyano-3-phenylpropyl)-$N^6$-trifluoroacetyl-L-lysine.

The internal standard analysis (internal standard: benzylhydantoin) obtained by using HPLC on the crystals showed that the purity was 92.4% and the isomer ratio of 1-(S) isomer to 1-(R) isomer was 91:9.

By recrystallizing 20 g of the crystals obtained from a mixture of 250 ml of methanol and 250 ml of water, 18.1 g of $N^2$-(1(S)-cyano-3-phenylpropyl)-$N^6$-trifluoroacetyl-L-lysine (purity 99%, SS ratio 99.7%) was obtained.

$^1$H—NMR (CDCl$_3$): δ: 1.33–2.3 (m, 8H), 2.67–3.06 (m, 2H), 3.17–3.83 (m, 4H), 5.42–6.4 (m, 1H), 7.08–7.49 (m, 5H), 8.0–8.37 (m, 1H).

IR (cm$^{-1}$, KBr, disk): 3300, 2940, 1700, 1560, 1180, 1160, 700.

EXAMPLE 2

Synthesis of $N^2$-(1(S)-cyano-3-phenylpropyl)-$N^6$-trifluoroacetyl-L-lysine-N-carboxy Anhydride In a 100 ml round bottom flask equipped with a reflux condenser were placed 3.7 g of $N^2$(1(S)-cyano-3-phenylpropyl)-$N^6$-trifluoroacetyl-L-lysine and 100 ml of a methylene chloride solution (0.6M) of phosgene and the mixture was refluxed for 15 hours. After the reaction was over, the greater part of methylene chloride (containing phosgene) was distilled off and then methylene chloride was completely removed under reduced pressure, whereby 3.9 g of $N^2$-(1(S)-cyano-3-phenylpropyl)-$N^6$-trifluoroacetyl-L-lysine-N-carboxy anhydride was obtained.

$^1$H—NMR (CDCl$_3$): δ: 1.1–2.17 (m, 6H), 2.17–2.6 (m, 2H), 2.6–3.03 (m, 2H), 3.12–3.53 (m, 2H), 4.14–5.0 (m, 2H), 6.71–7.6 (m, 6H).

IR (cm$^{-1}$, neat): 3350, 2930, 2250, 1860, 1780, 1720, 1560, 760.

EXAMPLE 3

Synthesis of $N^2$-(1(S)-cyano-3-phenylpropyl)-$N^6$-trifluoroacetyl-L-lysiyl-L-proline To a solution of 1.15 g of L-proline, 317 mg of sodium hydroxide, and 840 mg of sodium carbonate dissolved in 30 ml of water was added a solution of 4 g of $N^2$-(1(S)-cyano-3-phenylpropyl)-L-lysine-N-carboxy anhydride dissolved in 30 ml of acetone followed by stirring for one hour at 0° C. After adjusting the pH thereof to about 1 by adding 6N hydrochloric acid, the pH was adjusted to 4.2 by adding 1N sodium hydroxide and after distilling off acetone therefrom, the aqueous layer remained was extracted with ether. After drying the extracted ether layer by anhydrous sodium sulfate, the solvent was distilled off under reduced pressure to provide 4.3 g of $N^2$-(1(S)-cyano-3-phenylpropyl)-$N^6$-trifluoroacetyl-L-lysil-L-proline.

$^1$H—NMR (CDCl$_3$): δ: 1.27–2.4 (m, 12H), 2.53–3.0 (m, 2H), 3.08–3.93 (m, 6H), 4.33–4.67 (m, 1H), 5.83–6.34 (m, 2H), 6.98–7.52 (m, 6H).

IR (cm$^{-1}$, neat): 3300, 2950, 1720, 1640, 1455, 1190, 710.

EXAMPLE 4

Synthesis of $N^2$-(1(S)-carbamyl-3-phenylpropyl)-$N^6$-trifluoroacetyl-L-lysine After stirring a mixture of 12 g of $N^2$-(1(S)-cyano-3-phenylpropyl)-$N^6$-trifluoroacetyl-L-lysine and 40 ml of concentrated hydrochloric acid for 5 hours at room temperature, 200 ml of ice-water was added thereto and after adjusting the pH thereof to about 4.5 with an aqueous sodium hydroxide solution with stirring, the mixture was stirred for 30 minutes at 0° C. The crystals thus deposited were washed with water, recovered by filtration, and dried in vacuo at 45° C. to provide 8.3 g of $N^2$-(1(S)-carbamyl-3-phenylpropyl)-$N^6$-trifluoroacetyl-L-lysine.

$^1$H—NMR (CDCl$_3$, DMSOd$_6$): δ: 1.3–2.13 (m, 3H), 2.53–2.87 (m, 3H), 3.10–3.45 (m, 5H), 4.15 (br s, 2H), 7.0–7.42 (m, 6H).

IR (cm$^{-1}$, KBr, disk): 3400, 3200, 1700, 1680, 1620, 1550, 1190.

EXAMPLE 5

Synthesis of $N^2$-(1(S)-carbamyl-3-phenylpropyl)-$N^6$-trifluoroacetyl-L-lysine-N-carboxy anhydride In a 100 ml round bottom flask equipped with a reflux condenser were placed 4 g of $N^2$-(1(S)-carbamyl-3-phenylpropyl)-$N^6$-trifluoroacetyl-L-lysine and 100 ml of a methylene chloride solution (0.6M) of phosgene followed by refluxing for 15 hours. After the reaction was over, the greater part of methylene chloride (containing phosgene) was distilled off and further methylene chloride was completely removed under reduced pressure, whereby 8.7 g of $N^2$-(1(S)-carbamyl-3-phenylpropyl)-$N^6$-trifluoroacetyl-L-lysine-N-carboxy anhydride was obtained.

$^1$H—NMR (CDCl$_3$,): δ: 1.0–3.62 (m, 16H), 3.8–4.73 (m, 2H), 6.67–7.53 (m, 6H).

IR (cm$^{-1}$, KBr, disk): 3300, 2930, 1845, 1780, 1610, 760, 700.

EXAMPLE 6

Synthesis of $N^2$-(1(S) carbamyl-3-phenylpropyl)-$N^6$-trifluoroacetyl-L-lysiyl-L-proline To a solution of 1.18 g of L-proline, 421 mg of sodium hydroxide, and 862 mg of sodium carbonate dissolved in 30 ml of water was added a solution of 3.7 g of $N^2$-(1(S)-carbamyl-3-phenylpropyl)-$N^6$-trifluoroacetyl-L-lysine-N-carboxy anhydride dissolved in 30 ml of acetone followed by stirring for one hour at 0° C. Then, after adjusting the pH of the mixture to about 4.5 by adding 1N sodium hydroxide, acetone was distilled off and the aqueous layer remained was washed with ether. After saturating the aqueous layer by the addition of sodium sulfate, the product was extracted with methylene chloride. The extract was dried by anhydrous sodium sulfate and then the solvent was distilled off under reduced pressure from the extract to provide 3.9 g of $N^2$-(1(S)-carbamyl-3-phenylpropyl)-$N^6$-trifluoroacetyl-L-lysiyl-L-proline.

$^1$H—NMR (CDCl$_3$, CD$_3$OD): δ: 1.27–2.33 (m, 12H), 2.5–2.93 (m, 4H), 3.07–3.67 (m, 6H), 4.33–4.52 (m, 1H), 7.1–7.33 (m, 6H).

IR (cm$^{-1}$, KBr, disk): 3300, 2960, 1650, 1465, 1230, 1200, 1175, 720.

EXAMPLE 7

Synthesis of
N$^2$-(1(S)-carbamyl-3-phenylpropyl)-N$^6$-trifluoroacetyl-L-lysil-L-proline To one gram of N$^2$-(1(S)-cyano-3-phenylpropyl)-N$^6$-trifluoroacetyl-L-lysil-L-proline were added 35 ml of 25N sulfuric acid and 5 ml of ethanol at 0° C. followed by stirring for 10 hours at 0° C. and after adding thereto 100 ml of water while cooling it well, the pH was adjusted to about 4.5 with 6N sodium hydroxide. The reaction product formed was washed with 100 ml of ether, extracted thrice each with 100 ml of methylene chloride, the extract was dried over anhydrous sodium sulfate, and then the solvent was distilled off to provide 720 ml of N$^2$-(1(S)-carbamyl-3-phenylpropyl)-N$^6$-trifluoroacetyl-L-lysil-L-proline.

EXAMPLE 8

Synthesis of
N$^2$-(1(S)-ethoxycarbonyl-3-phenylpropyl)-N$^6$-trifluoroacetyl-L-lysine To 2 g of N$^2$-(1(S)-cyano-3-phenylpropyl)-N$^6$-trifluoroacetyl-L-lysine was added 40 ml of 6N dry HCl/ethanol at 0° C. followed by stirring for 20 hours at 0° C. and after adding thereto 100 ml of ice water, the resultant mixture was stirred for 30 minutes. After adjusting the pH of the mixture to about 4.5 with an aqueous sodium hydroxide solution, the reaction mixture was extracted with methylene chloride. The extract was dried by anhydrous sodium sulfate and the solvent was distilled off under reduced pressure to provide an oily product. The oily product thus obtained was separated by silica gel column chromatograph (eluate: butanol/acetic acid/water=30/3/1) to provide 162 mg of crystals of N$^2$-(1(S)-ethoxycarbonyl-3-phenylpropyl)-N$^6$-trifluoroacetyl-L-lysine.

$^1$H—NMR (CDCl$_3$): δ: 1.3 (t, 3H, J=7Hz), 1.42–2.25 (m, 8H), 2.5–2.85 (m, 2H), 3.0–3.55 (m, 4H), 4.17 (q, 2H, J=7Hz), 5.4–5.83 (br. s, 2H), 6.9–7.4 (m, 6H).

IR (cm$^{-1}$, KBr, disk): 3320, 1740, 1700, 1615, 1205, 1170, 750, 700.

m.p.: 137.0° to 138.0° C.

[α]$_D^{25}$=7.0° (c=2, ethanol).

EXAMPLE 9

Synthesis of
N$^2$-(1(S)-ethoxycarbonyl-3-phenylpropyl)-L-lysine-N-carboxy anhydride In a 100 ml round bottom flask equipped with a reflux condenser were placed N$^2$-(1(S)-ethoxycarbonyl-3-phenylpropyl)-L-lysine and 20 ml of an aqueous methylene chloride solution (0.6M soln.) of phosgene and the mixture was refluxed for 15 hours. After the reaction was over, the greater part of methylene chloride (containing phosgene) was distilled off and then methylene chloride was completely removed under reduced pressure to provide 0.92 g of N$^2$-(1(S)-ethoxycarbonyl-3-phenylpropyl)-L-lysine-N-carboxy anhydride.

$^1$H—NMR (CDCl$_3$): δ: 1.3 (t, 3H, J=7Hz), 1.16–2.13 (m, 8H), 2.24–2.6 (m, 2H), 2.62–2.98 (m, 2H), 3.14–3.57 (m, 2H), 4.0–4.43 (m, 4H), 6.6–7.0 (m, 1H), 7.12–7.56 (m, 5H).

IR (cm$^{-1}$, KBr, disk): 3350, 2870, 1855, 1780, 1740, 1710, 1560, 1190, 950.

EXAMPLE 10

Synthesis of
N$^2$-(1(S)-ethoxycarbonyl-3-phenylpropyl)-N$^6$-trifluoroacetyl L-lysil-L-proline To a solution of 393 g of L-proline, 137 mg of sodium hydroxide, and 287 mg of sodium carbonate dissolved in 10 ml of water was added a solution of 782 g of N$^2$-(1(S)-ethoxycarbonyl-3-phenylpropyl)-N$^6$-trifluoroacetyl-L-lysine-N-carboxy anhydride dissolved in 10 ml of acetone and the mixture was stirred for one hour at 0° C. After adjusting the pH thereof to about 1 by adding 6N hydrochloric acid, the pH thereof was adjusted to 4.5 by the addition of 1N aqueous sodium hydroxide solution, acetone was distilled off from the solution, and aqueous layer thus formed was extracted by methylene chloride. After drying the extracted by anhydrous sodium sulfate, the solvent was distilled off under reduced pressure to provide 832 g of N$^2$-(1(S)-ethoxycarbonyl-3-phenylpropyl)-N$^6$-trifluoroacetyl-L-lysil-L-proline as an oily product. The oily product thus obtained was dissolved in 5.5 ml of t-butyl methyl ether by heating to 40° C. and after cooling the solution to 5° C. for 20 hours, the crystals thus deposited were diluted with 2 ml of cyclohexane followed by stirring for one hour. The crystals thus obtained were recovered by filtration, washed with a small amount of cyclohexane, and dried in vacuo at room temperature to provide 647 mg of the crystals of N$^2$-(1(S)-ethoxycarbonyl-3phenylpropyl)-N$^6$-trifluoroacetyl-L-lysil L-proline.

m.p.: 74.5° to 76.5° C.

[α]$_D^{25}$=−15.4° (c=1.0, methanol/0.1N HCl (1/1)).

$^1$H—NMR (CDCl$_3$): δ: 1.28 (t, 3H, J=7Hz), 1.4–2.83 (m, 12H), 2.57–2.67 (m, 2H), 3.1–3.73 (m, 6H), 4.13 (q, 2H, J=7Hz), 4.35–4.63 (m, 1H), 6.37 (br. s, 1H), 7.0–7.68 (m, 6H).

EXAMPLE 11

Synthesis of
N$^2$-(1(S)-carbonyl-3-phenylpropyl)-L-lysil-L-proline

To 10 ml of 6N sulfuric acid was added 1 g of N$^2$-(1(S)-carbanyl-3-phenylpropyl)-N$^6$-trifluoroacetyl-L-lysil-L-proline followed by stirring for 15 hours at 80° C., after cooling the mixture to 0° C., 50 ml of water was added thereto and after adjusting the pH thereof to 5.5 with 2N aqueous sodium hydroxide solution, and then adjusting the pH to 7.5 with 1N ammonium hydroxide, the volatile matters were distilled off. To the residue formed was added to 10 ml of ethanol, insoluble inorganic salts were filtered off, and after concentrated the filtrate under reduced pressure, the residual solids were purified by LH-20 chromatography (methanol) to provide 632 mg of N$^2$-(1(S)-carboxy-3-phenylpropyl)-L-lysil-L-proline as solids. The properties of the product coincided with those described in Journal of Pharmaceutical Science, 74, 352 (1985).

EXAMPLE 12

Synthesis of
N$^2$-(1(S)-carboxy-3-phenylpropyl)-L-lysil-L-proline

To a mixture of 5 ml of ethanol, 10 ml of water, and 25 ml of concentrated sulfuric acid was added 1 g of N$^2$-(1(S)-cyano-3-phenylpropyl)-N$^6$-trifluoroacetyl-L-lysil-L-proline followed by stirring for 45 minutes at room temperature. To the reaction mixture was added 115 ml of water and the mixture was refluxed for 24 hours at 80° C. The reaction was over, the pH thereof was adjusted to 7.5 with aqueous 5N ammonium hydroxide solution, the volatile matters were distilled off, and the residue formed was purified as in Example 11 to provide 320 mg of N$^2$-(1(S)-carboxy-3-phenylpropyl)-L-lysil-L proline.

While the invention has been described in detail and with reference to specific embodiments thereof, it will be apparent to one skilled in the art that various changes and modifications can be made therein without departing from the spirit and scope thereof.

What is claimed is:

1. A process for producing N$^2$-(1-(S)-carboxy-3-phenylpropyl)-L-lysil-L-proline of the formula

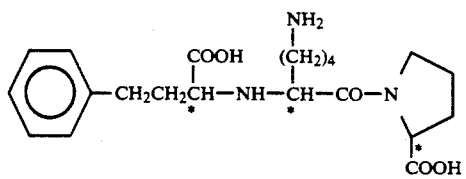

wherein * represents an asymmetric carbon atoms of the (S) configuration,
which comprises reacting an N$^2$-(1-substituted-3-phenylpropyl)-L-lysine-N-carboxy anhydride of the formula

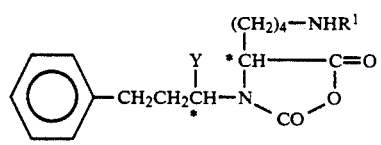

wherein R$^1$ represents an isobornyloxycarbonyl group, a trifluoroacetyl group, a formyl group, a phthaloyl group, a tertbutyloxycarbonyl group, a benzyloxycarbonyl group of a p-nitrobenzyloxycarbonyl group; Y represents a cyano group, a carbamoyl group, or an alkoxycarbonyl group of formula COOW, wherein W represents an alkyl group having from 1 to 4 carbon atoms, and * has the same meaning given above,
with L-proline or a derivative thereof of the formula

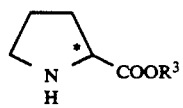

wherein R$^3$ represents a hydrogen atom, a alkyl group, or an aralkyl group; and * has the same meaning given above, in the presence of a base, to obtain an N$^2$-(1-substituted-3-phenylpropyl)-L-lysil-L-proline compound of the formula (VII);

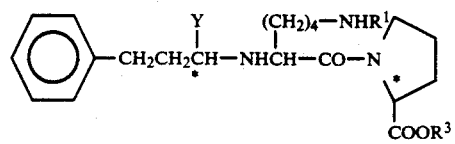

wherein R$^1$, R$^3$, Y and * have the same meaning given above;
and hydrolyzing the N$^2$-(1-substituted-3-phenylpropyl)-L-lysil-L-proline compound with an acid when Y is cyano or carbonyl, or with a base when Y is alkoxycarbonyl.

2. A process for producing an N$^2$-(1-substituted-3-phenylpropyl)-L-lysil-L-proline compound of the formula

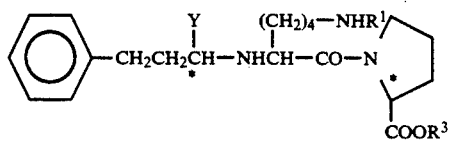

wherein R$^1$ represents an isobornyloxycarbonyl group, a trifluoroacetyl group, a formyl group, a phthaloyl group, a tertbutoxycarbonyl group, a benzyloxycarbonyl group, or a p-nitrobenzloycarbonyl group;
Y represents a cyano group, a carbamoyl group, or a alkoxycarbonyl group of formula COOW, wherein W represents an alkyl group having from 1 to 4 carbon atoms;
R$^3$ represents a hydrogen atom, an alkyl group, or an aralkyl group;
and * represents an asymmetric carbon atom of the (S) configuration,
which comprises reacting an N$^2$-(1-substituted-3-phenylpropyl)-L-lysine compound of the formula

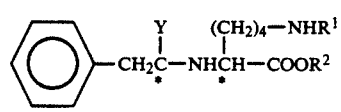

wherein R$^2$ represents a hydrogen atom, an alkyl group, or an aralkyl group; and R$^1$, Y and * have the same meanings given above,
after hydrolysis or hydrogenolysis when R$^2$ represents an alkyl group or an aralkyl group, with phosgene or trichloromethyl chloroformate, to provide an N$^2$-(1-substituted-3-phenyl-propyl)-L-lysine-N-carboxy anhydride of the formula

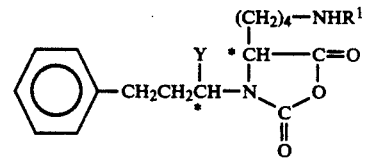

wherein R$^1$, Y and * have the same meanings given above;
and reacting the N-carboxy anhydride, in the presence of a base, with L-proline or a derivative thereof of the formula

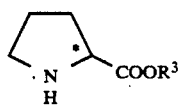

wherein R³ and * have the same meanings given above.

3. The process according to claim 2, wherein the N²-(1-substituted-3-phenylpropyl)-L-lysine compound in which Y represents ethoxycarbonyl group and having the formula $$\text{C}_6\text{H}_5\text{—CH}_2\text{CH}_2\text{—}\overset{*}{\underset{\text{COOC}_2\text{H}_5}{\text{CH}}}\text{—NH—}\overset{*}{\underset{(\text{CH}_2)_4\text{—NHR}^1}{\text{CH}}}\text{—COOR}^2$$

is obtained by reacting an N²-(1-cyano-3-phenylpropyl)-L-lysine compound of the formula $$\text{C}_6\text{H}_5\text{—CH}_2\text{CH}_2\text{—}\overset{*}{\underset{\text{CN}}{\text{CH}}}\text{—NH—}\overset{*}{\underset{(\text{CH}_2)_4\text{NHR}^1}{\text{CH}}}\text{—COOR}^2$$

in an ethanol solution of hydrogen chloride at a temperature of from $-30°$ C. to $30°$ C. to form an imidate, and hydrolyzing the imidate.

4. The process according to claim 2, wherein the N²-(1-substituted-3-phenylpropyl)-L-lysine compound in which Y represents a carbonyl group and having the formula $$\text{C}_6\text{H}_5\text{—CH}_2\text{CH}_2\text{—}\overset{*}{\underset{\text{CONH}_2}{\text{CH}}}\text{—NH}\overset{*}{\underset{(\text{CH}_2)_4\text{NHR}^1}{\text{CH}}}\text{—COOR}^2$$

is obtained by hydrolyzing an N²-(1-cyano-3-phenylpropyl)-L-lysine compound of the formula $$\text{C}_6\text{H}_5\text{—CH}_2\text{CH}_2\text{—}\overset{*}{\underset{\text{CN}}{\text{CH}}}\text{—NH—}\overset{*}{\underset{(\text{CH}_2)_4\text{NHR}^1}{\text{CH}}}\text{—COOR}^2$$

with a mineral acid at a temperature of from $-10°$ C. to $80°$ C.

5. The process according to claim 3, wherein the N²-(1-cyano-3-phenylpropyl)-L-lysine compound is obtained by reacting β-phenylpropionaldehyde with an L-lysine compound of the formula $$\text{H}_2\text{N}\overset{*}{\underset{(\text{CH}_2)_4\text{NHR}^1}{\text{CH}}}\text{—COOR}_2$$

in the presence of a cyanating agent in a protonic solvent at a temperature of from $-40°$–$80°$ C.; and isolating the 1-(S) lysine compound.

6. The process according to claim 4, wherein the compound N²-(1-cyano-3-phenylpropyl-L-lysine is obtained by reacting β-phenylpropionaldehyde with an L-lysine compound of the formula $$\text{H}_2\text{N}\overset{*}{\underset{(\text{CH}_2)_4\text{NHR}^1}{\text{CH}}}\text{—COOR}_2$$

wherein * represents an asymmetric carbon atom of the (S) configuration, and isolating the 1-(S) lysine compound.

7. The process for preparing an N²-(1-carbonyl-3-phenylpropyl)-L-lysil-L-proline compound of the formula $$\text{C}_6\text{H}_5\text{—CH}_2\text{CH}_2\overset{*}{\underset{\text{CONH}_2}{\text{CH}}}\text{—NH—}\overset{*}{\underset{(\text{CH}_2)_4}{\underset{|}{\text{CH}}}\overset{\text{NHR}^1}{|}}\text{—CO—N}\underset{\overset{*}{\text{COOR}^3}}{\diagdown}$$

wherein R¹ represents an isobornyloxycarbonyl group, a trifluoroacetyl group, a formyl group, a phthaloyl group, a tertbutoxycarbonyl group, a benzloyxcarbonyl group, or a p-nitrobenzyloxycarbonyl group;
R³ represents a hydrogen atom, an alkyl group, or an aralkyl group;
and * represents an asymmetric carbon atom of the (S) configuration, which comprises reacting an N²-(1-cyano-3-phenylpropyl)-L-lysine compound of the formula $$\text{C}_6\text{H}_5\text{—CH}_2\text{CH}_2\text{—}\overset{*}{\underset{\text{CN}}{\text{CH}}}\text{—NH—}\overset{*}{\underset{(\text{CH}_2)_4\text{—NHR}^1}{\text{CH}}}\text{—COOR}^2$$

wherein R² represent a hydrogen atom, an alkyl group, or an aralkyl group, with phosgene to produce an N²-(1-cyano-3-phenylpropyl)-L-lysine-N-carboxy anhydride of the formula $$\text{C}_6\text{H}_5\text{—CH}_2\text{CH}_2\text{—}\overset{*}{\underset{\text{CN}}{\text{CH}}}\text{—N}\underset{\underset{\text{O}}{\overset{|}{\text{C}}}\underset{\text{O}}{\diagdown}\underset{\text{O}}{\overset{|}{\text{C}}}}{\diagdown}\overset{*}{\underset{(\text{CH}_2)_4\text{—NHR}^1}{\text{CH}}}$$

and reacting the N-carboxy anhydride with L-proline or a derivative thereof of the formula $$\underset{\text{H}}{\text{N}}\diagdown\overset{*}{\text{COOR}^3}$$

in the presence of a base to obtain an N²-(1-cyano-3-phenylpropyl)-L-lysil-L-proline compound of the formula $$\text{C}_6\text{H}_5\text{—CH}_2\text{CH}_2\text{—}\overset{*}{\underset{\text{CN}}{\text{CH}}}\text{—NH—}\overset{*}{\underset{(\text{CH}_2)_4}{\underset{|}{\text{CH}}}\overset{\text{NR}^1}{|}}\text{—CO—N}\underset{\overset{*}{\text{COOR}^3}}{\diagdown}$$

and hydrolyzing the N²-(1-cyano-3-phenylpropyl)-L-lysil-L-proline compound with an acid.

* * * * *